United States Patent
Hyde et al.

(10) Patent No.: US 9,682,241 B2
(45) Date of Patent: Jun. 20, 2017

(54) INTRUSION RESISTANT IMPLANTABLE MEDICAL DEVICE

(75) Inventors: Roderick A. Hyde, Redmond, WA (US); Muriel Y. Ishikawa, Livermore, CA (US); Eric C. Leuthardt, St. Louis, MO (US); Michael A. Smith, Phoenix, AZ (US); Lowell L. Wood, Jr., Bellevue, WA (US)

(73) Assignee: GEARBOX, LLC, Bellevue, WA (US)

( * ) Notice: Subject to any disclaimer, the term of this patent is extended or adjusted under 35 U.S.C. 154(b) by 2186 days.

(21) Appl. No.: 12/150,933

(22) Filed: Apr. 30, 2008

(65) Prior Publication Data
US 2009/0276011 A1 Nov. 5, 2009

Related U.S. Application Data

(63) Continuation-in-part of application No. 12/150,934, filed on Apr. 30, 2008.

(51) Int. Cl.
*A61N 1/372* (2006.01)
*A61N 1/08* (2006.01)
*A61N 1/37* (2006.01)

(52) U.S. Cl.
CPC ........... *A61N 1/37247* (2013.01); *A61N 1/08* (2013.01); *A61N 1/37* (2013.01); *A61N 1/37252* (2013.01); *A61N 1/37258* (2013.01)

(58) Field of Classification Search
CPC ................. A61N 1/37252; A61N 1/37258
USPC ........................................ 607/27, 30, 31, 60
See application file for complete search history.

(56) References Cited

U.S. PATENT DOCUMENTS

| | | | |
|---|---|---|---|
| 7,044,911 B2 | 5/2006 | Drinan et al. | |
| 7,060,031 B2 | 6/2006 | Webb et al. | |
| 7,127,299 B2 | 10/2006 | Nelson et al. | |
| 7,198,603 B2 | 4/2007 | Penner et al. | |
| 7,225,031 B2 | 5/2007 | Feliss et al. | |
| 7,231,251 B2 | 6/2007 | Yonce et al. | |
| 2002/0123673 A1 | 9/2002 | Webb et al. | |
| 2003/0004403 A1 | 1/2003 | Drinan et al. | |
| 2003/0078631 A1 | 4/2003 | Nelson et al. | |
| 2003/0172940 A1 | 9/2003 | Rogers et al. | |

(Continued)

OTHER PUBLICATIONS

"Antivirus Defense-in-Depth Guide"; Microsoft TechNet; bearing dates of May 20, 2004 and Aug. 25, 2004; pp. 1-11; Microsoft.com; located at http://www.microsoft.com/technet/security/guidance/serversecurity/avdind_2.mspx?pf=true; printed on Mar. 19, 2008.

(Continued)

*Primary Examiner* — Tammie K Heller
(74) *Attorney, Agent, or Firm* — Faisal K. Abou-Nasr; Advent, LLP

(57) ABSTRACT

A medical apparatus is disclosed, at least a portion of which is configured for implantation in an animal. The medical apparatus includes a communication module configured to receive communications originating external to the animal. The medical apparatus also includes a threat assessment module configured to ascertain a malware threat characteristic of a communication received by the communication module. The medical apparatus further includes a threat mitigation module configured to implement a mitigation measure responsive to the ascertained malware threat characteristic of the received communication.

37 Claims, 11 Drawing Sheets

(56) References Cited

U.S. PATENT DOCUMENTS

| | | |
|---|---|---|
| 2004/0088012 A1 | 5/2004 | Kroll et al. |
| 2004/0116981 A1 | 6/2004 | Mazar |
| 2004/0162591 A1 | 8/2004 | Jorgenson et al. |
| 2004/0204744 A1 | 10/2004 | Penner et al. |
| 2005/0101843 A1 | 5/2005 | Quinn et al. |
| 2005/0203582 A1* | 9/2005 | Healy et al. .................. 607/31 |
| 2005/0245995 A1 | 11/2005 | Diebold |
| 2005/0251227 A1 | 11/2005 | Khoo et al. |
| 2005/0283198 A1 | 12/2005 | Haubrich et al. |
| 2005/0288736 A1 | 12/2005 | Persen et al. |
| 2005/0288737 A1 | 12/2005 | Feliss et al. |
| 2006/0009813 A1 | 1/2006 | Taylor et al. |
| 2006/0030904 A1 | 2/2006 | Quiles |
| 2006/0189854 A1 | 8/2006 | Webb et al. |
| 2006/0212092 A1 | 9/2006 | Pless et al. |
| 2006/0212097 A1 | 9/2006 | Varadan et al. |
| 2006/0253005 A1 | 11/2006 | Drinan et al. |
| 2007/0043399 A1 | 2/2007 | Stevenson et al. |
| 2007/0060800 A1 | 3/2007 | Drinan et al. |
| 2007/0123949 A1 | 5/2007 | Dabney et al. |
| 2007/0142728 A1 | 6/2007 | Penner et al. |
| 2007/0210923 A1 | 9/2007 | Butler et al. |
| 2007/0219594 A1 | 9/2007 | Yonce et al. |
| 2007/0233204 A1 | 10/2007 | Lima et al. |
| 2009/0048644 A1* | 2/2009 | Stahmann et al. .............. 607/60 |

OTHER PUBLICATIONS

Feder, Barnaby J.; "A Heart Device Is Found Vulnerable to Hacker Attacks"; The New York Times; dated Mar. 12, 2008; pp. 1-2; The New York Times Company; Located at http://www.nytimes.com/2008/03/12/business/12heart-web.html?em=&en=1931a&ex=1205553600&pagewanted=print; printed on Mar. 13, 2008.

Leister, Wolfgang et al.; "Threat Assessment of Wireless Patient Monitoring Systems"; Norwegian Computing Center SAMPOS Project No. 176875; pp. 1; Located at http://publications.nr.no/SAMPOS-POSTER-2007.pdf.

* cited by examiner

Implementing in the implanted medical device a countermeasure responsive to the detected indication of malware in the received communication.

464 Implementing in the implanted medical device a countermeasure, the countermeasure responsive to the detected indication of malware in the received communication and meeting a minimum safety standard for the animal.

466 Implementing in the implanted medical device a countermeasure, the countermeasure responsive to the detected indication of malware in the received communication and predicted to meet a minimum safety standard for the animal.

468 Implementing in the implanted medical device a countermeasure, the countermeasure responsive to the detected indication of malware in the received communication and selected to provide a least adverse effect on the animal from among two countermeasures.

472 Implementing in the implanted medical device a countermeasure, the counter measure responsive to the ascertained threat characteristic of the received communication and predicted as unlikely to have an at least substantial adverse impact on the animal.

474 Implementing in the implanted medical device a countermeasure, the countermeasure responsive to the ascertained threat characteristic of the received communication and predicted by a lookup table as unlikely to have an at least substantial adverse impact on the animal.

476 Implementing in the implanted medical device a countermeasure, the countermeasure responsive to the detected indication of malware in the received communication and unlikely to cause an adverse reaction in the animal.

478 Implementing in the implanted medical device a countermeasure responsive to the detected indication of malware in the received communication and unlikely to have an at least substantially adverse impact on the medical device implanted in the animal.

FIG. 10

510 Computer-readable signal-bearing medium bearing the program instructions.

520 Program instructions configured to perform a process in a computing device of an animal-implantable medical apparatus, the process comprising:

receiving a communication originated by a source external to the animal;

detecting an indication of a malware in the received communication; and implementing in the implanted medical apparatus a countermeasure responsive to the detected indication of malware in the received communication.

522 Implementing in the implanted medical apparatus a countermeasure, the countermeasure selected in response to at least one of an algorithm or a lookup table and responsive to the detected indication of malware in the received communication.

524 Implementing in the implanted medical apparatus a countermeasure, the countermeasure responsive to the detected indication of malware in the received communication and unlikely to have an at least substantially adverse impact on the animal.

526 Implementing in the implanted medical apparatus a countermeasure responsive to the detected indication of malware in the received communication, and and meeting a minimum safety standard for the animal.

512 A computer readable storage medium bearing the program instructions.

514 A computer readable communication medium bearing the program instructions.

500 →

INTRUSION RESISTANT IMPLANTABLE MEDICAL DEVICE

RELATED APPLICATIONS

For purposes of the USPTO extra-statutory requirements, the present application constitutes a continuation-in-part of U.S. patent application Ser. No. 12/150,934, entitled SECURE OPERATION OF IMPLANTED DEVICE, naming Roderick A. Hyde, Muriel Y. Ishikawa, Eric C. Leuthardt, Michael A. Smith, and Lowell L. Wood, Jr. as inventors, filed Apr. 30, 2008, which is currently co-pending, or is an application of which a currently co-pending application is entitled to the benefit of the filing date.

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week 11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

SUMMARY

An embodiment provides a medical apparatus. At least a portion of the medical apparatus is configured for implantation in an animal. The medical apparatus includes a communication module configured to receive communications originating external to the animal. The medical apparatus also includes a threat assessment module configured to ascertain a threat characteristic of a communication received by the communication module. The medical apparatus further includes a threat mitigation module configured to implement a mitigation measure responsive to the ascertained threat characteristic of the received communication. In an alternative embodiment, the medical apparatus includes a patient module configured to engage a physiological aspect of the animal. In another embodiment, the medical apparatus includes a biocompatible housing adapted to be implanted in an animal. In another embodiment, the medical apparatus also includes a power source providing operational power to at least a portion of the medical apparatus. In another embodiment, the medical apparatus includes a backdoor module configured to respond to a command received from a trusted or a verified third party without regard to the implemented mitigation measure responsive to the ascertained threat characteristic of the received communication. In addition to the foregoing, other embodiments are described in the claims, drawings, and text that form a part of the present application.

Another embodiment provides a method. The method is implemented in a medical apparatus implanted in an animal and configured to at least one of transmit or receive a communication originating external to the animal. The method includes receiving a communication. The method also includes detecting an indication of a malware in the received communication. The method further includes implementing in the implanted medical device a countermeasure responsive to the detected indication of malware in the received communication. In an alternative embodiment, the method further includes initiating a transmission of an attack notification in response to the indication of malware in the received communication. In addition to the foregoing, other embodiments are described in the claims, drawings, and text that form a part of the present application.

A further embodiment provides a computer program product. The computer program product includes a computer-readable signal-bearing medium bearing program instructions. The program instructions are configured to perform a process in a computing device of an animal-implantable medical apparatus. The process includes receiving a communication originated by a source external to the animal. The process also includes detecting an indication of a malware in the received communication. The process further includes implementing in the implanted medical apparatus a countermeasure responsive to the detected indication of malware in the received communication. In addition to the foregoing, other embodiments are described in the claims, drawings, and text that form a part of the present application.

An embodiment provides a medical device. The medical device is configured for implantation in a living subject. The medical device includes means for at least one of receiving or transmitting a communication outside of the living subject. The medical device also includes means for detecting an indication of a malware in a received communication. The medical device further includes means for implementing in an element of the implanted medical device a countermeasure responsive to the detected indication of malware in the received communication. In an alternative embodiment, the medical device further includes means for engaging a physiological aspect of the living subject. In addition to the foregoing, other embodiments are described in the claims, drawings, and text that form a part of the present application.

The foregoing summary is illustrative only and is not intended to be in any way limiting. In addition to the illustrative aspects, embodiments, and features described above, further aspects, embodiments, and features will

BRIEF DESCRIPTION OF THE DRAWINGS

FIG. 9 illustrates an alternative embodiment of the operational flow of FIG. 5;

FIG. 10 illustrates an example computer program product; and

DETAILED DESCRIPTION

Figure 1:
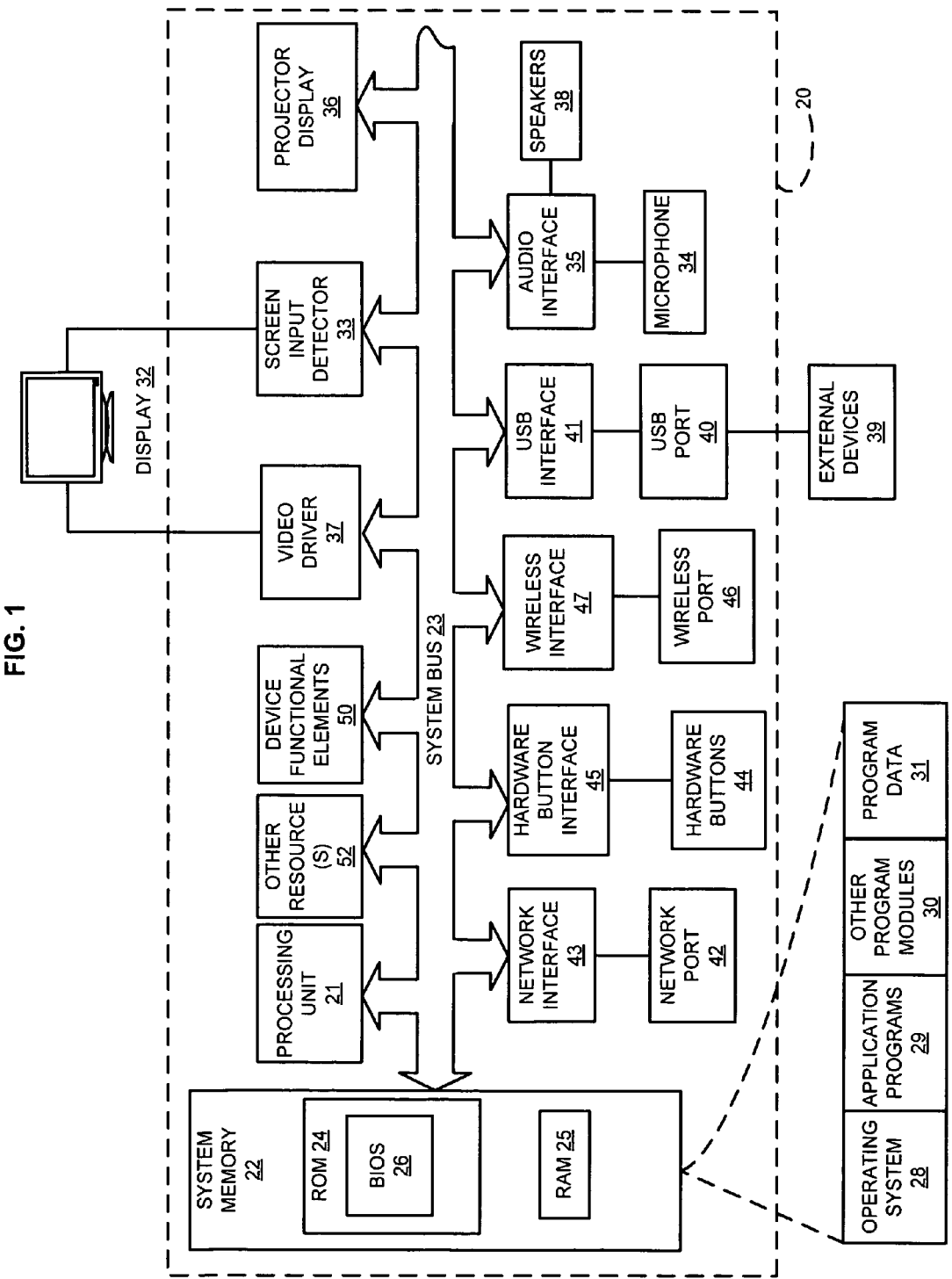
FIG. 1 illustrates an example embodiment of a thin computing device in which embodiments may be implemented.

In the following detailed description, reference is made to the accompanying drawings, which form a part hereof. In the drawings, similar symbols typically identify similar components, unless context dictates otherwise. The illustrated embodiments described in the detailed description, drawings, and claims are not meant to be limiting. Other embodiments may be utilized, and other changes may be made, without departing from the spirit or scope of the subject matter presented here.

FIG. 1 and the following discussion are intended to provide a brief, general description of an environment in which embodiments may be implemented. FIG. 1 illustrates an example system that includes a thin computing device 20, which may be included in an electronic device that also includes a device functional element 50. For example, the electronic device may include any item having electrical and/or electronic components playing a role in a functionality of the item, such as a limited resource computing device, a wireless communication device, a mobile wireless communication device, an electronic pen, a handheld electronic writing device, a digital camera, a scanner, an ultrasound device, an x-ray machine, a non-invasive imaging device, a cell phone, a PDA, a Blackberry® device, a printer, a refrigerator, a car, and an airplane. In another example, the thin computing device may be included in an implantable medical apparatus or device. In a further example, the thin computing device may be operable to communicate with an implantable or implanted medical apparatus.

The thin computing device 20 includes a processing unit 21, a system memory 22, and a system bus 23 that couples various system components including the system memory 22 to the processing unit 21. The system bus 23 may be any of several types of bus structures including a memory bus or memory controller, a peripheral bus, and a local bus using any of a variety of bus architectures. The system memory includes read-only memory (ROM) 24 and random access memory (RAM) 25. A basic input/output system (BIOS) 26, containing the basic routines that help to transfer information between sub-components within the thin computing device 20, such as during start-up, is stored in the ROM 24. A number of program modules may be stored in the ROM 24 and/or RAM 25, including an operating system 28, one or more application programs 29, other program modules 30 and program data 31.

A user may enter commands and information into the computing device 20 through input devices, such as a number of switches and buttons, illustrated as hardware buttons 44, connected to the system via a suitable interface 45. Input devices may further include a touch-sensitive display with suitable input detection circuitry, illustrated as a display 32 and screen input detector 33. The output circuitry of the touch-sensitive display 32 is connected to the system bus 23 via a video driver 37. Other input devices may include a microphone 34 connected through a suitable audio interface 35, and a physical hardware keyboard (not shown). Output devices may include at least one the display 32, or a projector display 36.

In addition to the display 32, the computing device 20 may include other peripheral output devices, such as at least one speaker 38. Other external input or output devices 39, such as a joystick, game pad, satellite dish, scanner or the like may be connected to the processing unit 21 through a USB port 40 and USB port interface 41, to the system bus 23. Alternatively, the other external input and output devices 39 may be connected by other interfaces, such as a parallel port, game port or other port. The computing device 20 may further include or be capable of connecting to a flash card memory (not shown) through an appropriate connection port (not shown). The computing device 20 may further include or be capable of connecting with a network through a network port 42 and network interface 43, and through wireless port 46 and corresponding wireless interface 47 may be provided to facilitate communication with other peripheral devices, including other computers, printers, and so on (not shown). It will be appreciated that the various components and connections shown are examples and other components and means of establishing communication links may be used.

The computing device 20 may be primarily designed to include a user interface. The user interface may include a character, a key-based, and/or another user data input via the touch sensitive display 32. The user interface may include using a stylus (not shown). Moreover, the user interface is not limited to an actual touch-sensitive panel arranged for directly receiving input, but may alternatively or in addition respond to another input device such as the microphone 34. For example, spoken words may be received at the microphone 34 and recognized. Alternatively, the computing device 20 may be designed to include a user interface having a physical keyboard (not shown).

The device functional elements 50 are typically application specific and related to a function of the electronic device, and is coupled with the system bus 23 through an interface (not shown). The functional elements may typically perform a single well-defined task with little or no user configuration or setup, such as a refrigerator keeping food cold, a cell phone connecting with an appropriate tower and transceiving voice or data information, a camera capturing and saving an image, an implantable medical apparatus.

In certain instances, one or more elements of the thin computing device 20 may be deemed not necessary and omitted. In other instances, one or more other elements may be deemed necessary and added to the thin computing device.

Figure 2:
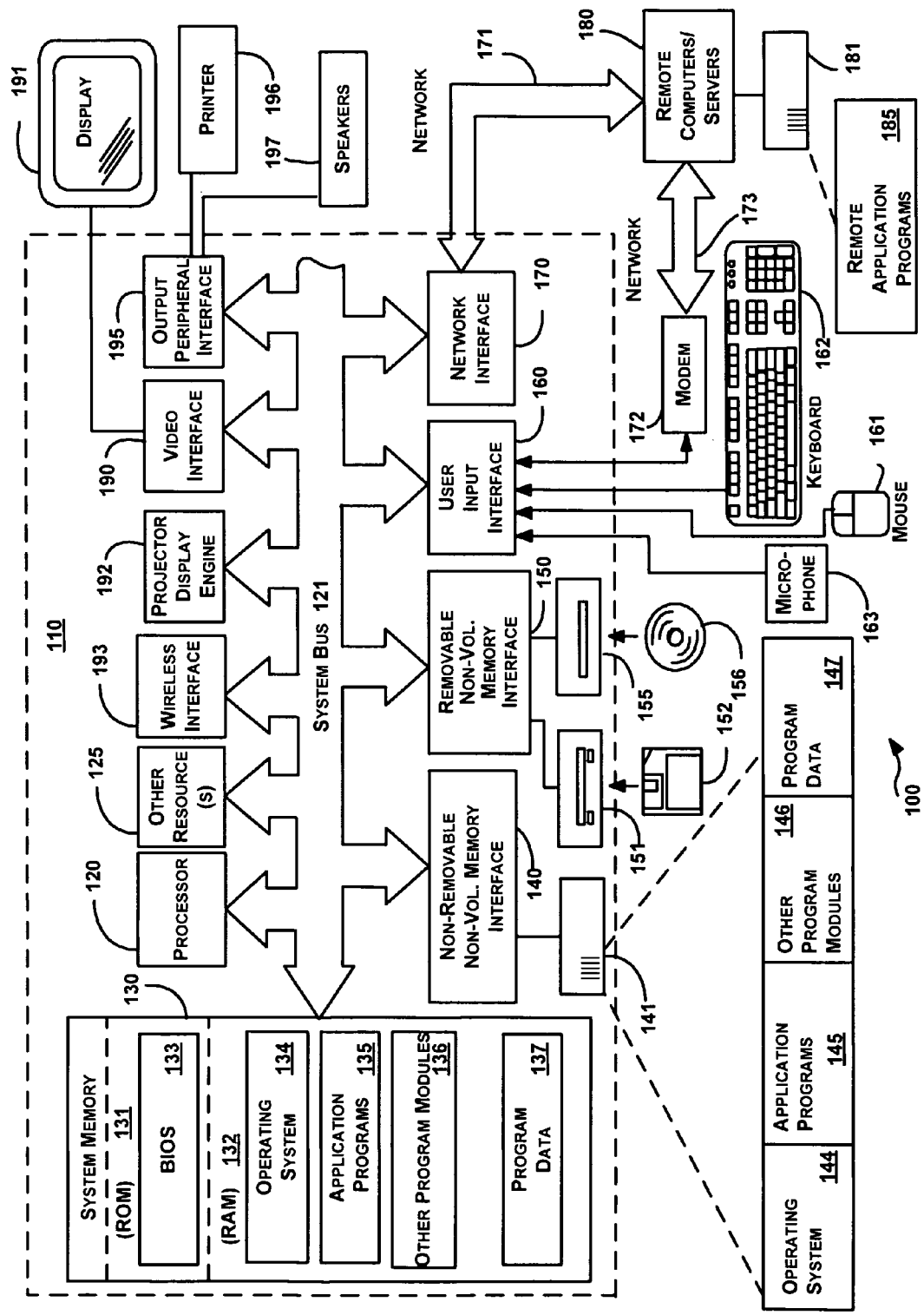
FIG. 2 illustrates an example embodiment of a general-purpose computing system in which embodiments may be implemented.

FIG. 2 illustrates an example embodiment of a general-purpose computing system in which embodiments may be implemented, shown as a computing system environment 100. Components of the computing system environment 100 may include, but are not limited to, a computing device 110 having a processing unit 120, a system memory 130, and a system bus 121 that couples various system components including the system memory to the processing unit 120. The system bus 121 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, also known as Mezzanine bus.

The computing system environment 100 typically includes a variety of computer-readable media products. Computer-readable media may include any media that can be accessed by the computing device 110 and include both volatile and nonvolatile media, removable and non-removable media. By way of example, and not of limitation, computer-readable media may include computer storage media and communication media.

Computer storage media includes volatile and nonvolatile, removable and non-removable media implemented in any method or technology for storage of information such as computer-readable instructions, data structures, program modules, or other data. Computer storage media includes, but is not limited to, random-access memory (RAM), read-only memory (ROM), electrically erasable programmable read-only memory (EEPROM), flash memory, or other memory technology, CD-ROM, digital versatile disks (DVD), or other optical disk storage, magnetic cassettes, magnetic tape, magnetic disk storage, or other magnetic storage devices, or any other medium which can be used to store the desired information and which can be accessed by the computing device 110. In a further embodiment, a computer storage media may include a group of computer storage media devices. In another embodiment, a computer storage media may include an information store. In another embodiment, an information store may include a quantum memory, a photonic quantum memory, and/or atomic quantum memory. Combinations of any of the above may also be included within the scope of computer-readable media.

Communication media may typically embody computer-readable instructions, data structures, program modules, or other data in a modulated data signal such as a carrier wave or other transport mechanism and include any information delivery media. The term "modulated data signal" means a signal that has one or more of its characteristics set or changed in such a manner as to encode information in the signal. By way of example, and not limitation, communication media include wired media, such as a wired network and a direct-wired connection, and wireless media such as acoustic, RF, optical, and infrared media.

The system memory 130 includes computer storage media in the form of volatile and nonvolatile memory such as ROM 131 and RAM 132. A RAM may include at least one of a DRAM, an EDO DRAM, a SDRAM, a RDRAM, a VRAM, and/or a DDR DRAM. A basic input/output system (BIOS) 133, containing the basic routines that help to transfer information between elements within the computing device 110, such as during start-up, is typically stored in ROM 131. RAM 132 typically contains data and program modules that are immediately accessible to or presently being operated on by processing unit 120. By way of example, and not limitation, FIG. 2 illustrates an operating system 134, application programs 135, other program modules 136, and program data 137. Often, the operating system 134 offers services to applications programs 135 by way of one or more application programming interfaces (APIs) (not shown). Because the operating system 134 incorporates these services, developers of applications programs 135 need not redevelop code to use the services. Examples of APIs provided by operating systems such as Microsoft's "WINDOWS" are well known in the art.

The computing device 110 may also include other removable/non-removable, volatile/nonvolatile computer storage media products. By way of example only, FIG. 2 illustrates a non-removable non-volatile memory interface (hard disk interface) 140 that reads from and writes for example to non-removable, non-volatile magnetic media. FIG. 2 also illustrates a removable non-volatile memory interface 150 that, for example, is coupled to a magnetic disk drive 151 that reads from and writes to a removable, non-volatile magnetic disk 152, and/or is coupled to an optical disk drive 155 that reads from and writes to a removable, non-volatile optical disk 156, such as a CD ROM. Other removable/nonremovable, volatile/non-volatile computer storage media that can be used in the example operating environment include, but are not limited to, magnetic tape cassettes, memory cards, flash memory cards, DVDs, digital video tape, solid state RAM, and solid state ROM. The hard disk drive 141 is typically connected to the system bus 121 through a non-removable memory interface, such as the interface 140, and magnetic disk drive 151 and optical disk drive 155 are typically connected to the system bus 121 by a removable non-volatile memory interface, such as interface 150.

The drives and their associated computer storage media discussed above and illustrated in FIG. 2 provide storage of computer-readable instructions, data structures, program modules, and other data for the computing device 110. In FIG. 2, for example, hard disk drive 141 is illustrated as storing an operating system 144, application programs 145, other program modules 146, and program data 147. Note that these components can either be the same as or different from the operating system 134, application programs 135, other program modules 136, and program data 137. The operating system 144, application programs 145, other program modules 146, and program data 147 are given different numbers here to illustrate that, at a minimum, they are different copies.

A user may enter commands and information into the computing device 110 through input devices such as a microphone 163, keyboard 162, and pointing device 161, commonly referred to as a mouse, trackball, or touch pad. Other input devices (not shown) may include at least one of a touch sensitive display, joystick, game pad, satellite dish, and scanner. These and other input devices are often connected to the processing unit 120 through a user input interface 160 that is coupled to the system bus, but may be connected by other interface and bus structures, such as a parallel port, game port, or a universal serial bus (USB).

A display 191, such as a monitor or other type of display device or surface may be connected to the system bus 121 via an interface, such as a video interface 190. A projector display engine 192 that includes a projecting element may be coupled to the system bus. In addition to the display, the computing device 110 may also include other peripheral output devices such as speakers 197 and printer 196, which may be connected through an output peripheral interface 195.

The computing system environment 100 may operate in a networked environment using logical connections to one or more remote computers, such as a remote computer 180. The remote computer 180 may be a personal computer, a server, a router, a network PC, a peer device, or other common network node, and typically includes many or all of the elements described above relative to the computing device 110, although only a memory storage device 181 has been illustrated in FIG. 2. The network logical connections depicted in FIG. 2 include a local area network (LAN) and a wide area network (WAN), and may also include other networks such as a personal area network (PAN) (not shown). Such networking environments are commonplace in offices, enterprise-wide computer networks, intranets, and the Internet.

When used in a networking environment, the computing system environment 100 is connected to the network 171 through a network interface, such as the network interface 170, the modem 172, and/or the wireless interface 193. The network may include a LAN network environment, and/or a WAN network environment, such as the Internet. In a networked environment, program modules depicted relative to the computing device 110, or portions thereof, may be stored in a remote memory storage device. By way of example, and not limitation, FIG. 2 illustrates remote application programs 185 as residing on computer storage medium 181. It will be appreciated that the network connections shown are examples and other means of establishing communication link between the computers may be used.

In certain instances, one or more elements of the computing device 110 may be deemed not necessary and omitted. In other instances, one or more other elements may be deemed necessary and added to the computing device.

Figure 3:
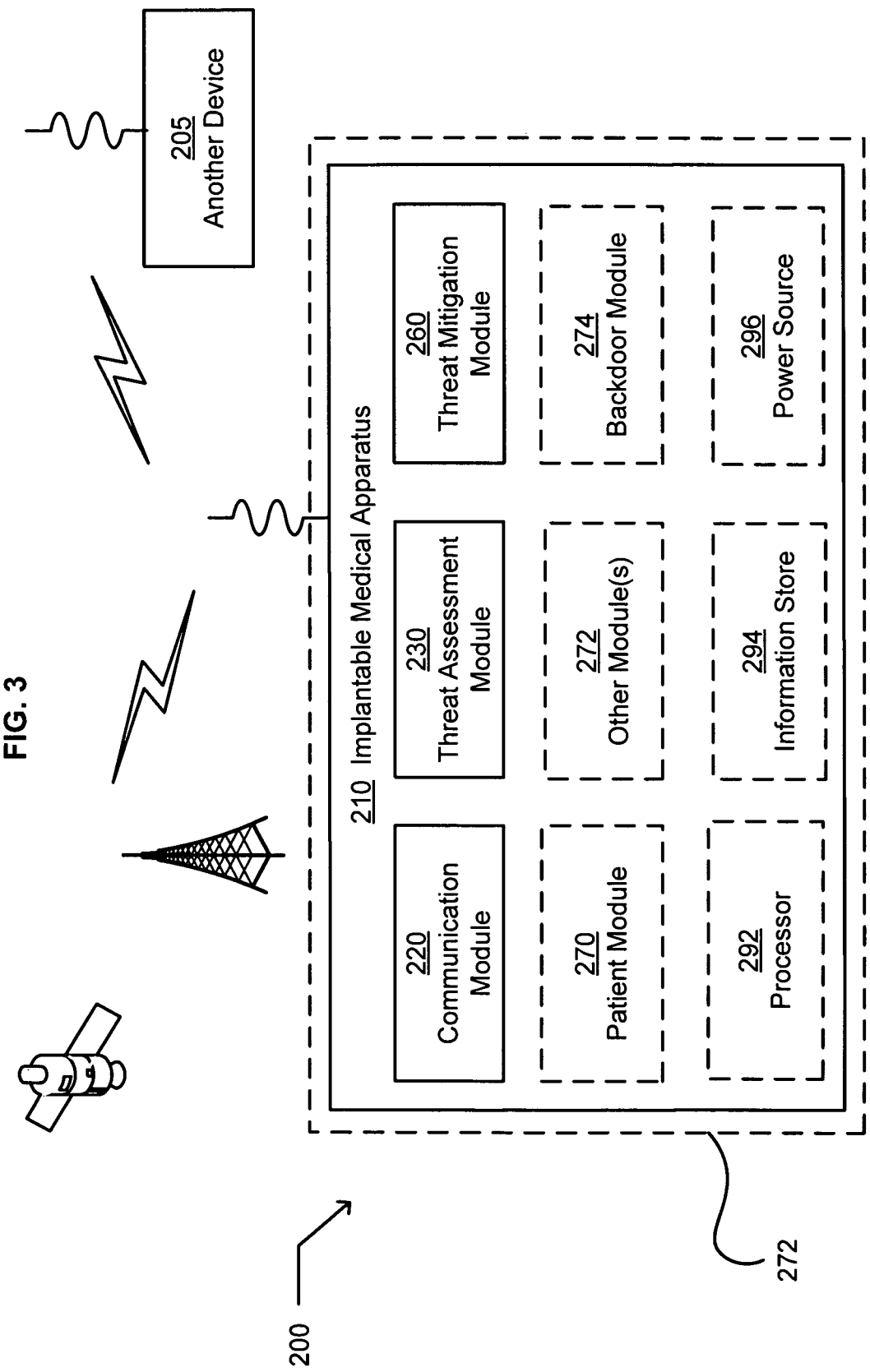
FIG. 3 illustrates an example environment in which embodiments may be implemented.

FIG. 3 illustrates an example environment 200 in which embodiments may be implemented. The environment includes a medical apparatus 210, at least a portion of which is configured for implantation in a patient. The environment may also include another device 205. The environment may also include a terrestrial or extraterrestrial communication link, illustrated as a communication tower and satellite. In an embodiment, the communication link may include at least one of a wired or a wireless communication link.

The medical apparatus 210 includes a communication module 220, a threat assessment module 230, and a threat mitigation module 260. The communication module includes a communication module configured to receive communications originated externally of the patient (not shown). For example, a communication originated externally of the patient may include a wireless signal originated by another device 205, such as a handheld version of the thin computing device 20 of FIG. 1, the computing device 110 of FIG. 2, a cell phone, or other communication originating device physically located outside of the patient.

The threat assessment module 230 includes a threat assessment module configured to ascertain a threat characteristic of a communication received by the communication module. In an embodiment, the communication received may include at least one of a received packet, file, data or information. In a further embodiment, the communication received may include at least one of a first communication received in an ordinary course of employing the medical apparatus and a second communication that includes a threat characteristic. In another embodiment, the communication received may include at least one of a signal or a modulated carrier. In a further embodiment, the communication received may include a communication received in at least one of an analog format or a digital format.

In an embodiment, a threat characteristic of the communication received may include at least one of a blocking communication, such as noise or a jamming, a failure to receive an expected communication, or an overwhelming communication, such as a denial of service attack. In a further embodiment, a threat characteristic of the communication received may include a spyware.

In another embodiment, a threat characteristic of the communication received may include an unauthorized or unregistered executable. In an embodiment, a threat characteristic of the communication received may include a malware. A malware may include malicious software. In another embodiment, a malware may include at least one of a virus, worm, or Trojan horse. In an embodiment, the threat characteristic may include an action the malware may perform on the medical apparatus 210, or on a computing device associated with the medical apparatus. In another embodiment, the threat characteristic may include an attack vector. In a further embodiment, the threat characteristic may include at least one of target environment, a carrier object, a transport mechanism, a payload, a trigger mechanism, or a defense mechanism. In another embodiment, a payload may include at least one of a backdoor, data corruption or deletion, information theft, denial of service, system shutdown, or service disruption.

In a further embodiment, ascertaining a threat characteristic may include identifying a malware present in the communication received. In another embodiment, ascertaining a threat characteristic may include identifying a malware present in the communication received, and finding the identified malware's threat characteristic in a look-up table stored in the implantable medical apparatus. In a further embodiment, ascertaining a threat characteristic may include identifying a malware present in the communication received, and obtaining the identified malware's threat characteristic from a device external to the animal. In an embodiment, the threat characteristic may be ascertaining using at least one of signature scanning, or heuristic scanning.

The threat mitigation module 260 includes a threat mitigation module configured to implement a mitigation measure responsive to the ascertained threat characteristic of the received communication.

In an alternative embodiment, the medical apparatus 210 may include a patient module 270 configured to engage a physiological aspect of the animal. In a further embodiment, the animal module includes a patient module configured to at least one of interact, relate, act, affect, effect, sense, or couple with a physiological aspect of the animal. For example, the patient module may be configured to acquire physiological signals from the heart, such as an electrocardiograph. In another example, the patient module may be configured to both sense and provide cardiac signals, such as with a cardiac pacemaker. In a further example, the patient module may be configured to acquire physiological signals from the central nervous system or the peripheral nervous system, such as with an EEG, or a NIR. In a further example, the patient module may be configured to monitor at least one of electrical changes, or changes in metabolism reflected by alterations in blood flow, glucose metabolism, or oxygen extraction. In another example, the patient module may be configured to monitor brain systems, and/or provide deep brain stimulation, cortical stimulation, vagus nerve stimulation, or spinal cord stimulation. In a further example, the patient module may be configured to monitor physiological conditions and/or changes in a limb, such as pulsoximetry, or blood or tissue pressure. In another example, the patient module may be configured to monitor an animal's metabolites, such as a glucose monitor. In another alternative embodiment, the patient module includes a patient module configured to sense a physiological aspect of the patient. For example, a sensed physiological aspect may include at least one of a sensed heart rate, heart pacing, acidity, blood chemistry such as pH, pCO2, pO2, blood component, activity state, or body temperature. In another example, the sensed physiological aspect may include at least one of a drug level, drug concentration, metabolite level, circulatory physiology such as blood pressure and cardiac output monitoring devices that communicate with ventricular assist devices to pump blood faster or slower, brain signal, perspiration, or movement.

In another embodiment, patient module 270 includes a patient module configured to provide a therapeutic benefit to the animal. For example, a provided therapeutic benefit may include at least one of providing a medicant, a medicine, a therapeutic substance, a drug eluted by a stent, a stimulation, a blocking, or a heart pacing. In a further embodiment, the patient module is configured to provide a therapeutic benefit by sensing a physiological aspect of the animal and communicating the sensed physiological aspect to an external device that in response provides or adjusts a therapeutic benefit. For example, physiological data may be acquired by the patient module and communicated using the communication module 220 with an external ventilator (not shown) configured to adjust at least one of the FI02, tidal volume, or rate of the breaths of the animal. In another example, the provided therapeutic benefit may include a non-drug approach, such at least one of an electrical, gastric, or mechanical approach.

In a further embodiment, the patient module 270 includes a patient module configured to engage at least a portion of a brain of the animal. For example, a neural implant, brain implant, or a neural modulator. In another embodiment, the patient module includes a neural modulator module configured to engage at least a portion of a nervous system of the animal. For example, a deep brain stimulator, neural interface, or nerve stimulator. In an embodiment, the patient module includes a patient module configured to acquire data indicative of a physiological aspect of the animal. In another embodiment, the patient module includes a control module configured to manage the patient module. In a further embodiment, the patient module includes a patient module configured to engage a physiological aspect of the animal and to monitor its own functioning. In another embodiment, the patient module includes a patient module configured to engage a physiological aspect of the animal during an implementation of the threat mitigation measure responsive to the ascertained threat characteristic of the received communication.

In an embodiment, the communication module 220 further includes a communication module configured to send and/or receive data having a relevance to the animal. In another embodiment, the communication module includes a communication module configured to receive communication originating external to the animal and configured to communicate with another medical apparatus configured for association with the animal. For example, the another medical apparatus configured for association with the animal may include another medical apparatus implanted in the animal. In a further embodiment, the communication module includes a communication module configured to receive communications originating external to the animal and to receive a communication useful in updating at least one of the threat assessment module or the threat mitigation module. In another embodiment, the threat assessment module includes a threat assessment module configured to ascertain a susceptibly of an implanted medical device to a threat characteristic of a communication received by the communication module.

In an embodiment, the threat assessment module 230 includes a threat assessment module configured to ascertain a threat characteristic of at least one of a fake communication, a spoofed communication, or a jamming communication received by the communication module. In another embodiment, the threat assessment module includes a threat assessment module configured to ascertain a threat characteristic of a communication received by the communication module and to initiate a notification to another apparatus of the ascertained threat characteristic. For example, the another apparatus may include at least one of another implantable or implanted medical apparatus, an external device or apparatus, or a health care provider. In a further embodiment, the threat assessment module includes a threat assessment module configured to be updatable in vivo and configured to ascertain a threat characteristic of a communication received by the communication module.

In another embodiment, the threat assessment module 230 includes a threat assessment module configured to ascertain a threat characteristic in response to a communication received by the communication module and in response to a history of previously ascertained threat characteristics. In a further embodiment, the threat assessment module includes a threat assessment module configured to store the ascertained threat characteristic. In another embodiment, the threat characteristic module includes a threat module configured to provide a stored ascertained threat characteristic in response to a query. In a further embodiment, the threat assessment module configured to ascertain a threat characteristic of a communication received by the communication module includes a threat assessment module configured to ascertain a presence of a threat characteristic of a communication received by the communication module and to ascertain a cessation of the ascertained threat characteristic In an embodiment, the threat mitigation module 260 includes a threat mitigation module configured to implement a selected mitigation measure responsive to the ascertained threat characteristic of the received communication. In another embodiment, the threat mitigation module includes a threat mitigation module configured to implement a mitigation measure responsive to the ascertained threat characteristic of the received communication and selected in response to a selection algorithm. In a further embodiment, the threat mitigation module includes a threat mitigation module configured to implement a mitigation measure selected based on a lookup table. For example, a mitigation measure may include establishing a safe mode in the medical apparatus 210. In another embodiment, the threat mitigation module includes a threat mitigation module configured to implement a mitigation measure selected according to a function dependent on at least one of a nature of the ascertained threat characteristic of the received communication, a remaining capability of a patient module of the medical apparatus to engage a physiological aspect of the animal, or a remaining life of a power source 274 providing operational power to the medical apparatus. For example, the nature of the ascertained threat characteristic may include an anticipated duration of a threat. By way of further example, a remaining capacity of the patient module may include an amount of medicant available for release in the animal.

In an embodiment, the threat mitigation module 260 includes a threat mitigation module configured to implement a mitigation measure responsive to the ascertained threat characteristic of the received communication, the mitigation measure including at least one of an encryption, an encryption change, a disinformation measure, a change of communication frequency, a change of a schedule of communication, a formatting of communication, a communication polarization, a handshake, tunneling, signature, authentication, or verification. In another embodiment, the threat mitigation module includes a threat mitigation module configured to be updated in vivo and configured to implement a mitigation measure responsive to the ascertained threat characteristic of the received communication. In a further embodiment, the threat mitigation module includes a threat mitigation module configured to implement a mitigation measure. The mitigation measure is responsive to the ascertained threat characteristic of the received communication and meeting a minimum safety standard for the animal.

In an embodiment, the threat mitigation module 260 includes a threat mitigation module configured to implement a mitigation measure in at least one of the patient module 270 or the communication module 220. The mitigation measure is responsive to the ascertained threat characteristic of the received communication and meeting a minimum safety standard for the animal.

In another embodiment, the threat mitigation module includes a threat mitigation module configured to implement a mitigation measure. The mitigation measure responsive to the ascertained threat characteristic of the received communication and predicted to meet a minimum safety standard for the animal. In a further embodiment, the threat mitigation module includes a threat mitigation module configured to implement a mitigation measure. The mitigation measure responsive to the ascertained threat characteristic of the received communication and selected to provide the least adverse effect on the animal from among two countermeasures. In an embodiment, the threat mitigation module includes a threat mitigation module configured to implement a mitigation measure responsive. The mitigation measure is responsive to the ascertained threat characteristic of the received communication and predicted by a lookup table as unlikely to have an at least substantial adverse impact on the animal. In another embodiment, the threat mitigation module includes a threat mitigation module configured to implement a mitigation measure. The mitigation measure is responsive to the ascertained threat characteristic of the received communication and predicted by a lookup table stored in the implanted medical apparatus as unlikely to have an at least substantial adverse impact on the animal. In a further embodiment, the threat mitigation module includes a threat mitigation module configured to implement a mitigation measure. The mitigation measure is responsive to the ascertained threat characteristic of the received communication and unlikely to have an at least substantially serious impact on the animal.

In another embodiment, the threat mitigation module 260 includes a threat mitigation module configured to implement a mitigation measure responsive to the ascertained threat characteristic of the received communication and to initiate a notification to another apparatus of the implemented mitigation measure. In a further embodiment, the threat mitigation module configured to implement a mitigation measure responsive to the ascertained threat characteristic of the received communication includes a threat mitigation module configured to reverse the implementation of the mitigation measure responsive. In an embodiment, the threat mitigation module configured to implement a mitigation measure responsive to the ascertained threat characteristic of the received communication includes a threat mitigation module configured to reverse the implementation of the mitigation measure and to initiate a notification to another apparatus of the reversing the implementation of the mitigation measure.

In another embodiment, the threat mitigation module configured to implement a mitigation measure responsive to the ascertained threat characteristic of the received communication includes a threat module configured to implement a mitigation measure responsive to the ascertained threat characteristic of the received communication and save an indication of the implemented mitigation measure. In further embodiment, the threat mitigation module configured to implement a mitigation measure responsive to the ascertained threat characteristic of the received communication includes a threat module configured to implement a mitigation measure responsive to the ascertained threat characteristic of the received communication and provide stored indication of the implemented mitigation measure in response to a query. In an embodiment, the threat mitigation module configured to implement a mitigation measure responsive to the ascertained threat characteristic of the received communication includes a threat module configured to implement a mitigation measure responsive to the ascertained threat characteristic of the received communication and a history that includes an ascertained threat characteristic of another received communication. In another embodiment, the threat mitigation module configured to implement a mitigation measure responsive to the ascertained threat characteristic of the received communication includes a threat module configured to implement a mitigation measure responsive to the ascertained threat characteristic of the received communication and a history that includes a previously implemented mitigation measure. In further embodiment, the threat mitigation module configured to implement a mitigation measure responsive to the ascertained threat characteristic of the received communication includes a threat module configured to implement a mitigation measure responsive to the ascertained threat characteristic of the received communication and an indication of a cessation of the ascertained threat characteristic.

In an embodiment, the medical apparatus 210 includes a biocompatible housing 272 adapted to be implanted in a mammalian patient (not shown). In another embodiment, the medical apparatus includes the power source 296 providing operational power to at least a portion of the medical apparatus. In another embodiment, the medical apparatus includes a backdoor module 274 configured to respond to a command received from a trusted or a verified third party without regard to the implemented mitigation measure responsive to the ascertained threat characteristic of the received communication. For example, the backdoor module may be configured to respond to a control command. By way of further example, the backdoor module may be configured to a command with respect to at least one of the patient module 270 or the medical apparatus as a whole. In a further embodiment, the medical apparatus may include at least one of other module(s) 272, processor 292, or an information store 294.

In an alternative embodiment, the medical apparatus 210 of FIG. 3 includes a medical apparatus at least a portion of which is configured for implantation in an animal. The medical apparatus 210 includes the communication module 220, the threat assessment module 230, and the threat mitigation module 260. The communication module includes a communication module configured to receive communications originating external to the medical apparatus. For example, a communication originating external to the medical apparatus may include another medical apparatus and/or device implanted in the animal (not shown).

Figure 4:
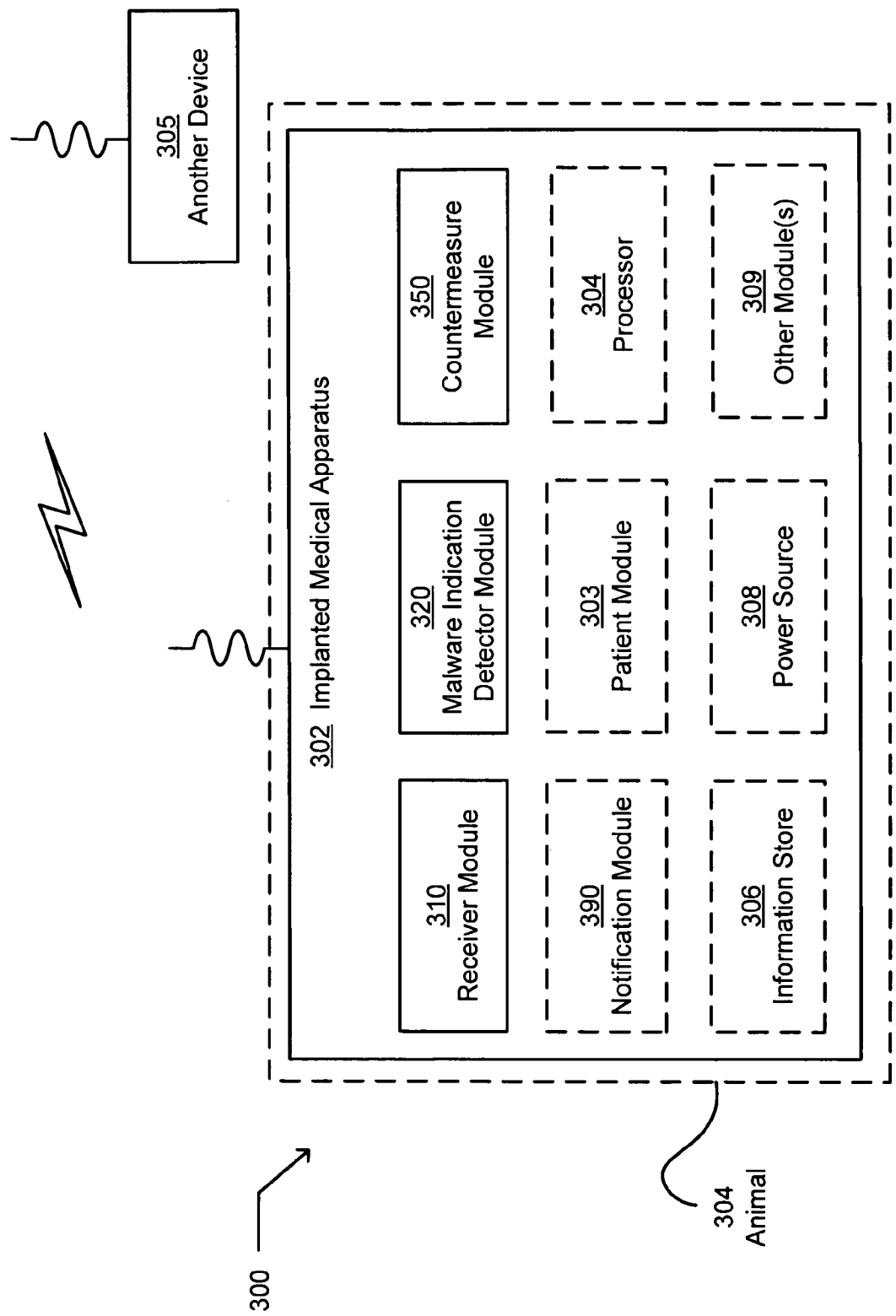
FIG. 4 illustrates another example environment in which embodiments may be implemented.

FIG. 4 illustrates another example environment 300 in which embodiments may be implemented. The example environment includes a medical apparatus 302 and another device 305. The medical apparatus is implanted in an animal 304. The medical apparatus includes a receiver module 310, a malware indication detector module 320, and a countermeasure module 350. In some embodiments, one or more of the receiver module, malware indication detector module, and countermeasure module may be structurally distinct from the remaining modules. In another embodiment, the electronic device or a portion of the medical apparatus may be implemented in whole or in part using the thin computing device 20 described in conjunction with FIG. 1, and/or the computing device 110 described in conjunction with FIG. 2. In a further embodiment, the medical apparatus or a portion of the medical apparatus may be implemented using Application Specific Integrated Circuits (ASICs), Field Programmable Gate Arrays (FPGAs), digital signal processors (DSPs), or other integrated formats. In a further embodiment, one or more of the modules, circuits and/or the apparatus may be implemented in hardware, software, and/or firmware.

The receiver module 310 includes a receiver module configured to at least one of transmit or receive a communication. In an alternative, embodiment, the receive module is configured to communicate externally to the animal, such as a communication with another device 305. The communication may be implemented using at least one of a wireless communication link or a wired communication link. The receiver module may be operable to communicate with the another device using a network, for example, such as the Internet or a private network. In another embodiment, the receiver module is configured to communicate externally to itself, such as with a second implanted medical apparatus or a device (not shown).

The medical apparatus 302 may include at least one additional module. The at least one additional module may include a notification module 390, a patient module 303, a processor 304, an information store 306, a power source 308, or other module(s) 309.

Figure 5:
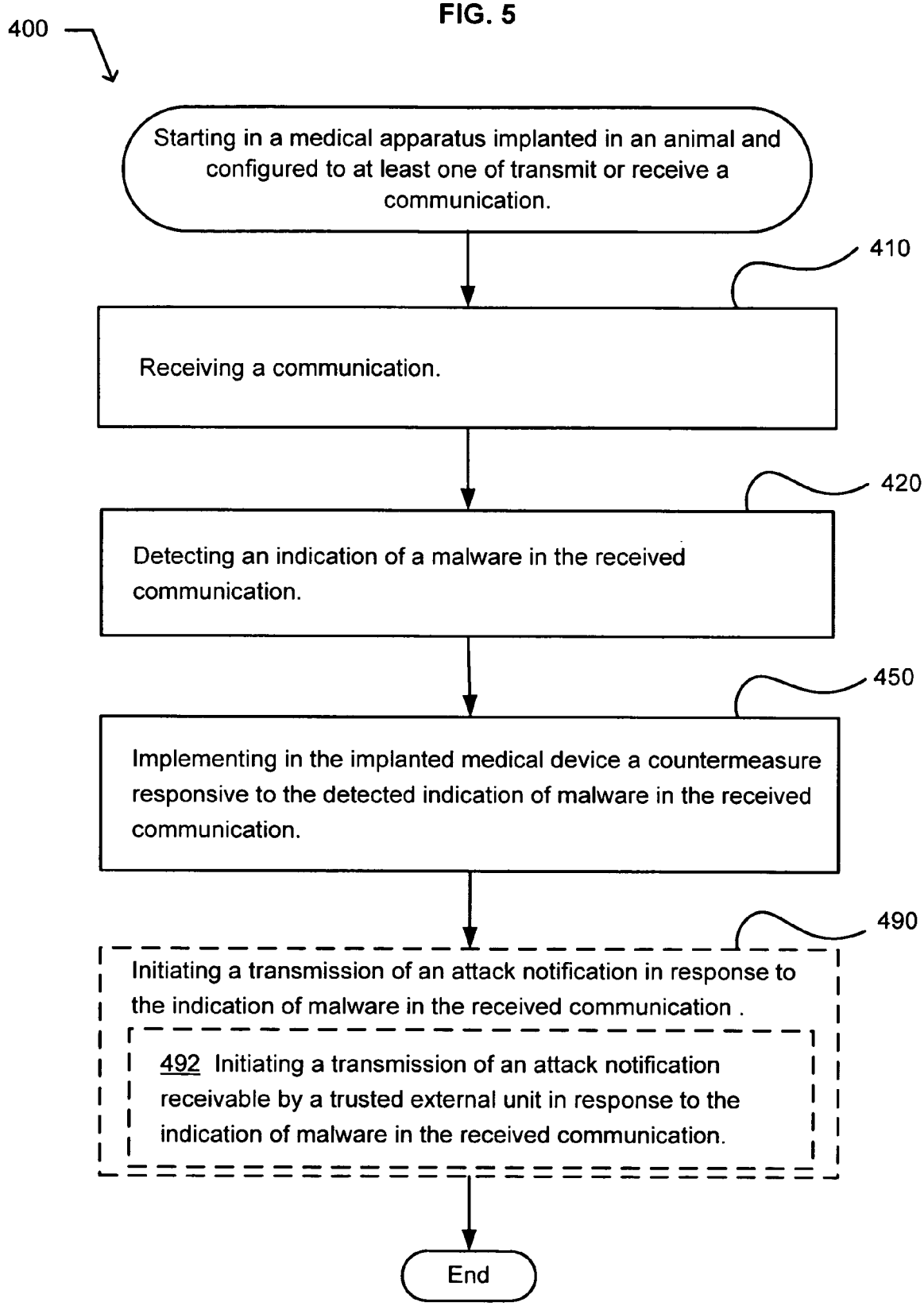
FIG. 5 illustrates an example of an operational flow implemented in an environment.

FIG. 5 illustrates an example of an operational flow 400 implemented in an environment. The environment includes a medical apparatus at least a portion of which is implanted in an animal and configured to at least one of transmit or receive a communication. In an embodiment, the medical apparatus may be adhered to the skin of the animal, or partially or wholly implanted in the animal. In another embodiment, the animal may include at least one of a patient, living body, human, animal, mammal, bird, fish, or food stock. The medical apparatus may be implemented using the medical apparatus 303 implanted in the animal 304 of FIG. 4. FIG. 5 and several following figures may include various examples of operational flows, discussions, and explanations with respect to the above-described environment 300 of FIG. 4, and/or with respect to other examples and contexts. However, it should be understood that the operational flows may be executed in a number of other environments and contexts, and/or in modified versions of FIG. 4. Also, although the various operational flows are illustrated in a sequence(s), it should be understood that the various operations may be performed in other orders than those which are illustrated, and/or may be performed concurrently.

After a start operation implemented in the environment that includes a medical apparatus implanted in an animal and configured to at least one of transmit or receive a communication, the operational flow 400 includes an acquirement operation 410. The acquirement operation includes receiving a communication. The acquirement operation may be implemented using the receiver module 310 of FIG. 4. A demodulation operation 420 includes detecting an indication of a malware in the received communication. In an embodiment, malware may include at least one of virus, a worm, Trojan horse, a rootkit, spyware, adware, a buffer overflow, a virus hoax, a dialer, or a hack tool. In another embodiment, a malware may include a program having a threat characteristic. The demodulation operation may be implemented using the malware indication detection module 320 of FIG. 4. A defense operation 450 includes implementing in the implanted medical device a countermeasure responsive to the detected indication of malware in the received communication. The defense operation may be implemented using the countermeasure module 350 of FIG. 4. The operational flow then proceeds to an end operation.

In an alternative embodiment, the operational flow 400 may include at least one additional operation. The at least one additional operation may include a notification operation 490. The notification operation includes initiating a transmission of an attack notification in response to the indication of malware in the received communication. In an alternative embodiment, the notification operation 490 includes an operation 492 initiating a transmission of an attack notification receivable by a trusted external unit in response to the indication of malware in the received communication. The trusted external unit may include the another device 305 of FIG. 4. The notification operation may be implemented using the notification module 390 of FIG. 4. In another embodiment, the notification operation includes initiating a secure transmission of an attack notification in response to the indication of malware in the received communication. In a further embodiment, the notification operation includes initiating a transmission of an indication of the countermeasure implemented in the implanted medical device.

Figure 6:
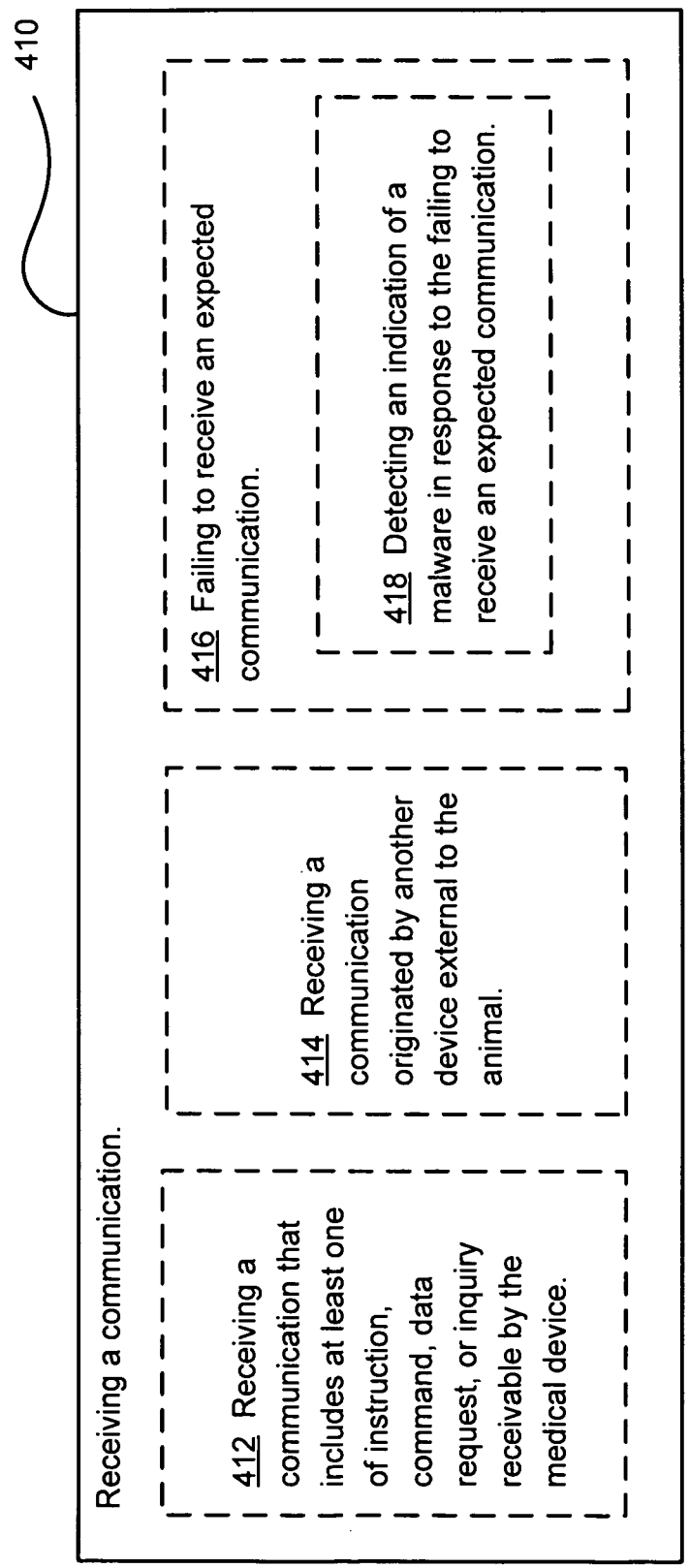
FIG. 6 illustrates an alternative embodiment of the operational flow of FIG. 5

FIG. 6 illustrates an alternative embodiment of the operational flow 400 of FIG. 5. The acquirement operation 410 may include at least one additional operation. The at least one additional operation may include at least one of an operation 412, an operation 414, or an operation 416. The operation 412 includes receiving a communication that includes at least one of instruction, command, data request, or inquiry receivable by the medical device. The operation 414 includes receiving a communication originated by another device external to the animal. The operation 416 includes failing to receive an expected communication. For example, failing to receive an expected communication may include at least one of failing to receive a handshake, an acknowledgement, or a scheduled communication. The operation 416 may include at least one additional operation, such as an operation 418. The operation 418 includes detecting an indication of a malware in response to the failing to receive an expected communication.

Figure 7:
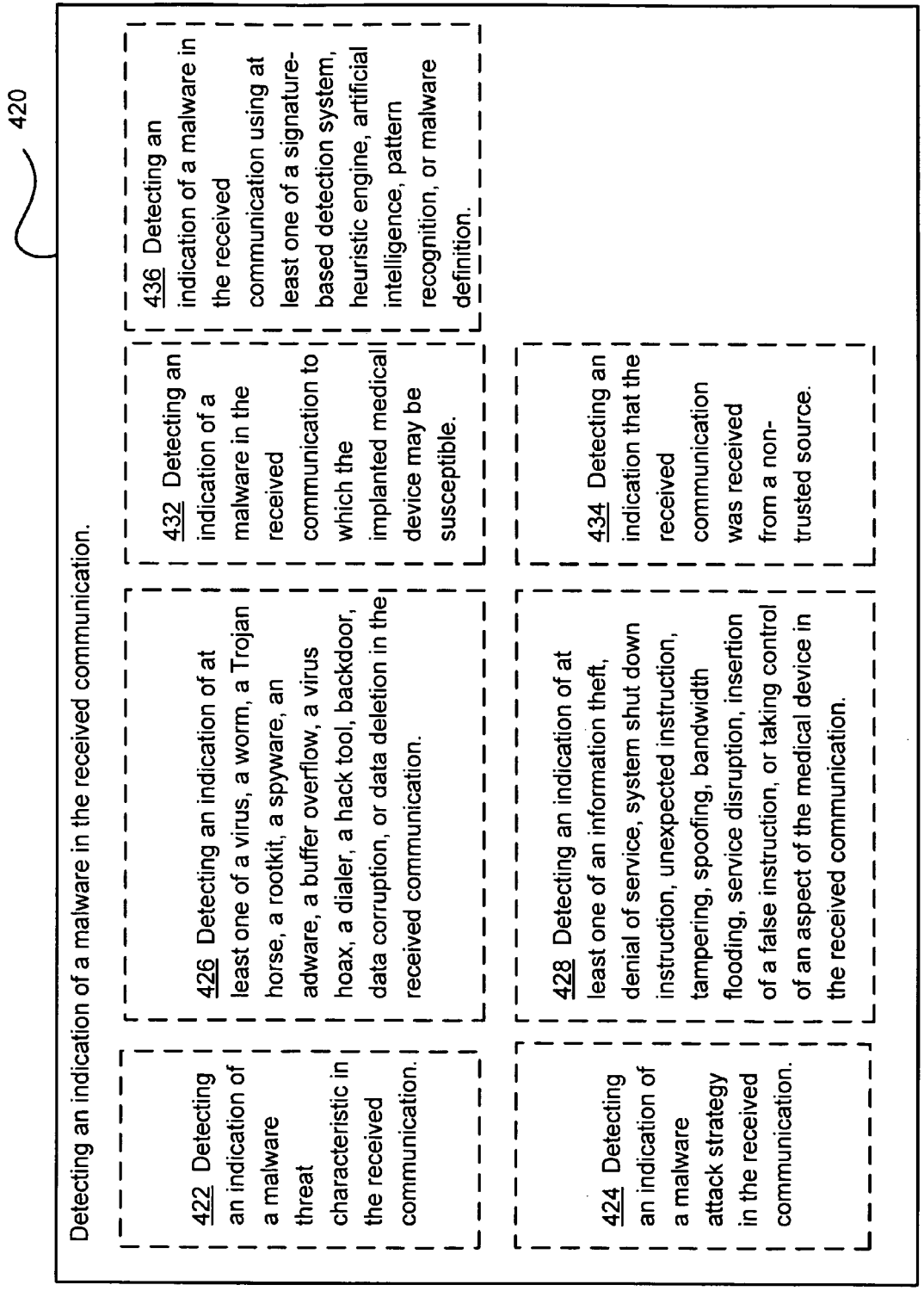
FIG. 7 illustrates another alternative embodiment of the operational flow of FIG. 5.

FIG. 7 illustrates another alternative embodiment of the operational flow 400 of FIG. 5. The demodulation operation 420 may include at least one additional operation. The at least one additional operation may include at least one of an operation 422, an operation 424, an operation 426, an operation 428, an operation 432, an operation 434, or an operation 436. The operation 422 includes detecting an indication of a malware threat characteristic in the received communication. The operation 424 includes detecting an indication of a malware attack strategy in the received communication. The operation 426 includes detecting an indication of at least one of a virus, a worm, a Trojan horse, a rootkit, a spyware, an adware, a buffer overflow, a virus hoax, a dialer, a hack tool, backdoor, data corruption, or data deletion in the received communication. The operation 428 includes detecting an indication of at least one of an information theft, denial of service, system shut down instruction, unexpected instruction, tampering, spoofing, bandwidth flooding, service disruption, insertion of a false instruction, or taking control of an aspect of the medical device in the received communication. The operation 432 includes detecting an indication of a malware in the received communication to which the implanted medical device may be susceptible. The operation 434 includes detecting an indication that the received communication was received from a non-trusted source. The operation 436 includes detecting an indication of a malware in the received communication using at least one of a signature-based detection system, heuristic engine, artificial intelligence, pattern recognition, or malware definition.

Figure 8:
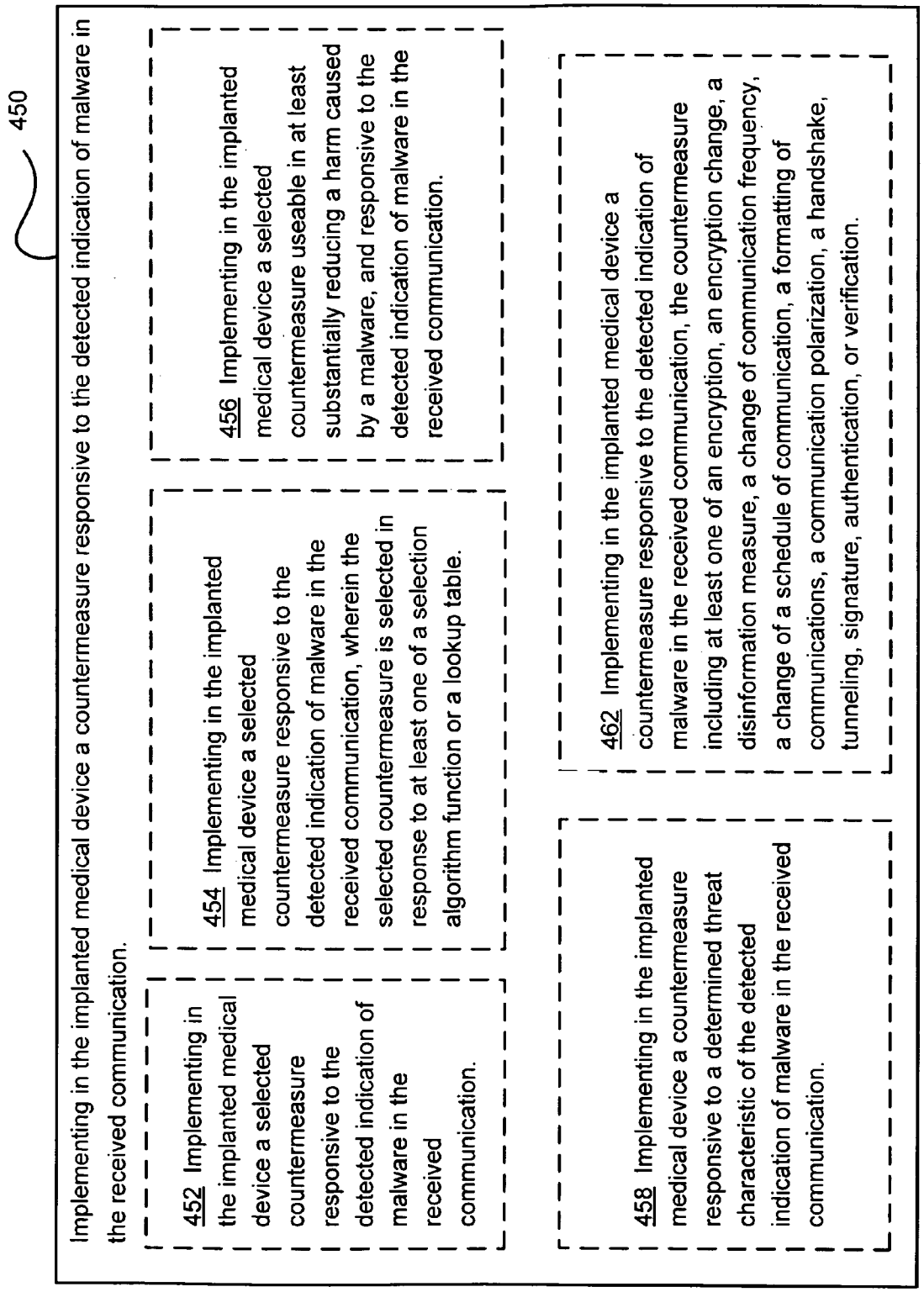
FIG. 8 illustrates a further alternative embodiment of the operational flow of FIG. 5.

FIG. 8 illustrates a further alternative embodiment of the operational flow 400 of FIG. 5. The defensive operation 450 may include at least one additional operation. The at least one additional operation may include at least one of an operation 452, an operation 454, an operation 456, an operation 458, and an operation 462. The operation 452 includes implementing in the implanted medical device a selected countermeasure responsive to the detected indication of malware in the received communication. The operation 454 includes implementing in the implanted medical device a selected countermeasure responsive to the detected indication of malware in the received communication, wherein the selected countermeasure is selected in response to at least one of a selection algorithm function or a lookup table. The operation 456 includes implementing in the implanted medical device a selected countermeasure useable in at least substantially reducing a harm caused by a malware, and responsive to the detected indication of malware in the received communication. The operation 458 includes implementing in the implanted medical device a countermeasure responsive to a determined threat characteristic of the detected indication of malware in the received communication. The operation 462 includes implementing in the implanted medical device a countermeasure responsive to the detected indication of malware in the received communication, the countermeasure including at least one of an encryption, an encryption change, a disinformation measure, a change of communication frequency, a change of a schedule of communication, formatting a communication, a communication polarization, a handshake, tunneling, signature, authentication, or verification.

FIG. 9 illustrates an alternative embodiment of the operational flow 400 of FIG. 5. The defensive operation 450 may include at least one additional operation. The at least one additional operation may include an operation 464. The operation 464 includes implementing in the implanted medical device a countermeasure. The countermeasure is responsive to the detected indication of malware in the received communication and meeting a minimum safety standard for the animal. The operation 464 may include at least one additional operation. The at least one additional operation may include an operation 466, an operation 468, an operation 472, an operation 474, an operation 476, or an operation 478. The operation 466 includes implementing in the implanted medical device a countermeasure. The countermeasure is responsive to the detected indication of malware in the received communication and predicted to meet a minimum safety standard for the animal. The operation 468 includes implementing in the implanted medical device a countermeasure. The countermeasure is responsive to the detected indication of malware in the received communication and selected to provide a least adverse effect on the animal from among two countermeasures. The operation 472 includes implementing in the implanted medical device a countermeasure. The counter measure is responsive to the ascertained threat characteristic of the received communication and predicted as unlikely to have an at least substantial adverse impact on the animal. The operation 474 includes in the implanted medical device a countermeasure. The countermeasure is responsive to the ascertained threat characteristic of the received communication and predicted by a lookup table as unlikely to have an at least substantial adverse impact on the animal. The operation 476 includes implementing in the implanted medical device a countermeasure. The countermeasure is responsive to the detected indication of malware in the received communication and unlikely to cause an adverse reaction in the animal. The operation 478 includes implementing in the implanted medical device a countermeasure. The countermeasure is responsive to the detected indication of malware in the received communication and unlikely to have an at least substantially adverse impact on the medical device implanted in the animal. In another embodiment, the operation 464 includes implementing in the implanted medical device a countermeasure. The countermeasure is responsive to the detected indication of malware in the received communication and unlikely to have an at least substantially adverse impact on an operation of the medical device implanted in the animal. In a further embodiment, the operation 464 includes implementing in the implanted medical device a countermeasure. The countermeasure is responsive to the detected indication of malware in the received communication and predicted by at least one of a prediction algorithm or a lookup table as unlikely to cause an adverse outcome to the animal.

FIG. 10 illustrates an example computer program product 500. The computer program product includes a computer-readable signal-bearing medium 510 bearing program instructions 520. The program instructions are configured to perform a process in a computing device of an animal-implantable medical apparatus. The process includes receiving a communication originated by a source external to the animal. The process also includes detecting an indication of a malware in the received communication. The process further includes implementing in the implanted medical apparatus a countermeasure responsive to the detected indication of malware in the received communication.

The program instructions 520 may include at least one alternative embodiment. The at least one alternative embodiment may include program instruction 522, a program instruction 524, or program instruction 526. Program instruction 522 includes implementing in the implanted medical apparatus a countermeasure. The countermeasure is selected in response to at least one of an algorithm or a lookup table and responsive to the detected indication of malware in the received communication. The lookup table may include a locally stored lookup table or a remotely stored lookup table. The program instruction 524 includes implementing in the implanted medical apparatus a countermeasure responsive to the detected indication of malware in the received communication, and predicted as unlikely to have an at least substantially adverse impact on the animal. In an embodiment, "predicted as unlikely" may include at least one of predicted as unlikely by a lookup table stored in the implanted medical apparatus, or by a selection algorithm. The program instruction 526 includes implementing in the implanted medical apparatus a countermeasure. The countermeasure is responsive to the detected indication of malware in the received communication and meeting a minimum safety standard for the animal.

In an alternative embodiment, the computer-readable signal-bearing medium 510 bearing the program instructions includes a computer readable storage medium 512 bearing the program instructions. In another alternative embodiment, the computer-readable signal-bearing medium bearing the program instructions includes a computer readable communication medium 514 bearing the program instructions.

Figure 11:
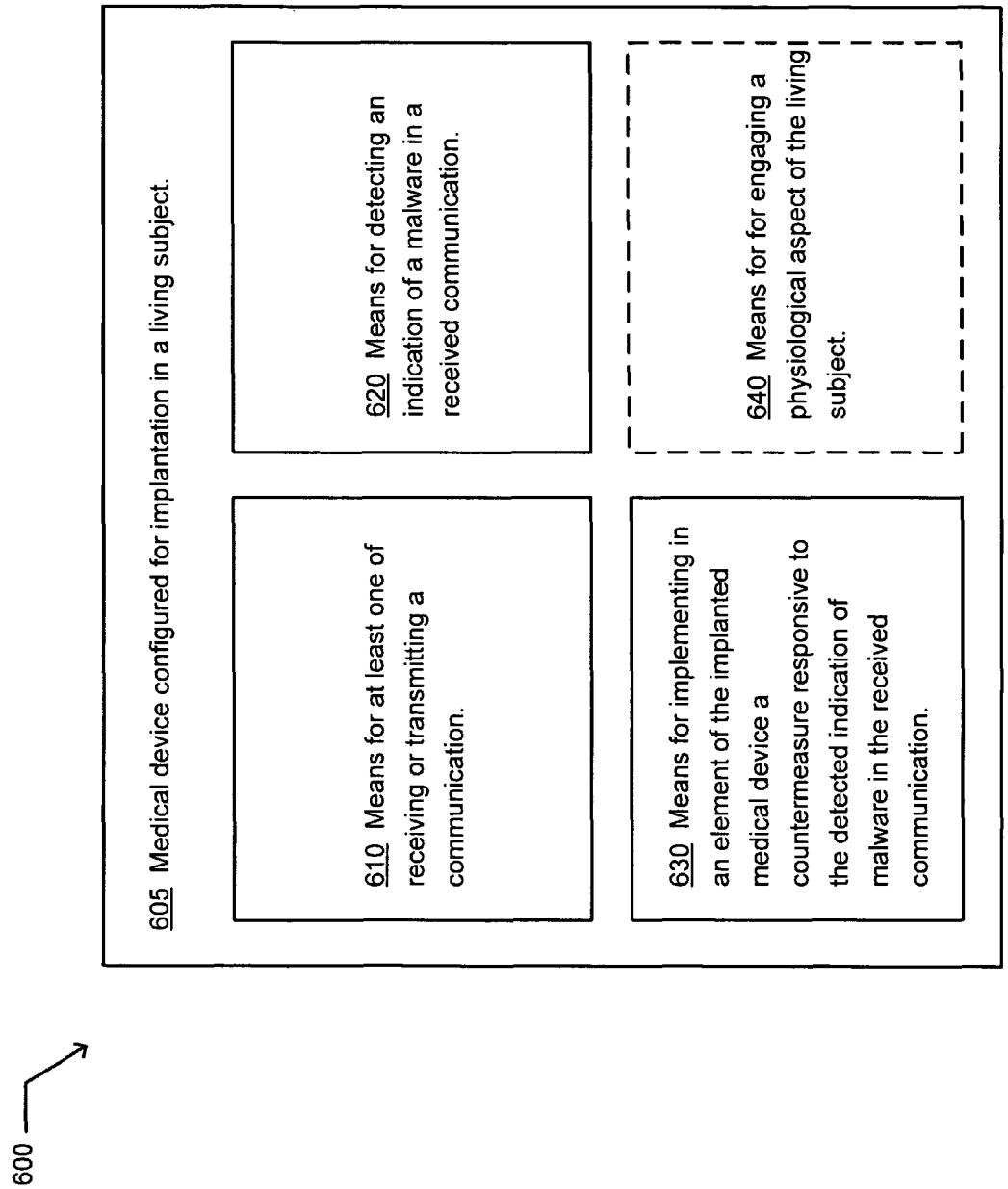
FIG. 11 illustrates an example system in which embodiments may be implemented.

FIG. 11 illustrates an example system 600 in which embodiments may be implemented. The system includes a medical device 605 configured for at least partial implantation in a living subject. The medical device includes means 610 for at least one of receiving or transmitting a communication. In an alternative embodiment, the means 610 is configured for receiving or transmitting outside of its self. In another embodiment, the means 610 is configured for receiving or transmitting outside of the living subject. The medical device further includes means 620 for detecting an indication of a malware in a received communication. The medical device further includes means 630 for implementing in an element of the implanted medical device a countermeasure responsive to the detected indication of malware in the received communication. In an alternative embodiment, the medical device includes means 640 for engaging a physiological aspect of the living subject.

The foregoing detailed description has set forth various embodiments of the systems, apparatus, devices, computer program products, and/or processes using block diagrams, flow diagrams, operation diagrams, flowcharts, illustrations, and/or examples. A particular block diagram, operation diagram, flowchart, illustration, environment, and/or example should not be interpreted as having any dependency or requirement relating to any one or combination of components illustrated therein. For example, in certain instances, one or more elements of an environment may be deemed not necessary and omitted. In other instances, one or more other elements may be deemed necessary and added.

Insofar as such block diagrams, operation diagrams, flowcharts, illustrations, and/or examples contain one or more functions and/or operations, it will be understood that each function and/or operation within such block diagrams, operation diagrams, flowcharts, illustrations, or examples can be implemented, individually and/or collectively, by a wide range of hardware, software, firmware, or virtually any combination thereof unless otherwise indicated. In an embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communication link, a wireless communication link, etc.).

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware. Those skilled in the art will recognize that optical aspects of implementations will typically employ optically-oriented hardware, software, and or firmware.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communication device (e.g., a modem, communication switch, or optical-electrical equipment). Those having skill in the art will recognize that the subject matter described herein may be implemented in an analog or digital fashion or some combination thereof.

In some embodiments, "configured" includes at least one of designed, set up, shaped, implemented, constructed, or adapted for at least one of a particular purpose, application, or function. In some embodiment, "module" includes a hardware, firmware, or software component that interacts with a larger system. In a further embodiment, a software module or program module may come in a form of a file and may typically handle a specific task within a larger software system. In another embodiment, a hardware module may include a unit that plugs into a larger system. In an embodiment, a module may be implemented in a circuit, such as in a software circuit or an electrical circuit. In another embodiment, a module may be implemented in hardware, software, firmware, or any combination thereof.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.).

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The herein described aspects depict different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality. Any two components capable of being so associated can also be viewed as being "operably couplable" to each other to achieve the desired functionality. Specific examples of operably couplable include but are not limited to physically mateable and/or physically interacting components and/or wirelessly interactable and/or wirelessly interacting components.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A medical apparatus at least a portion of which is configured for implantation in an animal, the medical apparatus comprising:
   a communication module configured to receive communications originating external to the animal;
   a threat assessment module configured to ascertain a malware threat characteristic of a communication received by the communication module; and
   a threat mitigation module configured to implement a mitigation measure responsive to the ascertained malware threat characteristic of the received communication.

2. The medical apparatus of claim 1, wherein the medical apparatus further includes:
   a patient module configured to engage a physiological aspect of the animal.

3. The medical apparatus of claim 2, wherein the patient module configured to engage a physiological aspect of the animal includes:
   a patient module configured to at least one of interact, relate, act, affect, effect, sense, or couple with a physiological aspect of the animal.

4. The medical apparatus of claim 2, wherein the patient module configured to engage a physiological aspect of the animal includes:
   a patient module configured to provide a therapeutic benefit to the animal.

5. The medical apparatus of claim 2, wherein the patient module configured to engage a physiological aspect of the animal includes:

a patient module configured to sense a physiological aspect of the animal.

6. The medical apparatus of claim 2, wherein the patient module configured to engage a physiological aspect of the animal includes:
a patient module configured to engage at least a portion of a brain of the animal.

7. The medical apparatus of claim 2, wherein the patient module configured to engage a physiological aspect of the animal includes:
a neural modulator module configured to engage at least a portion of a nervous system of the animal.

8. The medical apparatus of claim 2, wherein the patient module configured to engage a physiological aspect of the animal includes:
a patient module configured to acquire data indicative of a physiological aspect of the animal.

9. The medical apparatus of claim 2, wherein the patient module configured to engage a physiological aspect of the animal includes:
a control module configured to manage the patient module.

10. The medical apparatus of claim 2, wherein the patient module configured to engage a physiological aspect of the animal includes:
a patient module configured to engage a physiological aspect of the animal and to monitor its own functioning.

11. The medical apparatus of claim 2, wherein the patient module configured to engage a physiological aspect of the animal includes:
a patient module configured to engage a physiological aspect of the animal during an implementation of the threat mitigation measure responsive to the ascertained threat characteristic of the received communication.

12. The medical apparatus of claim 1, wherein the communication module configured to receive communications originating external to the animal includes:
a communication module configured to receive communications originating external to the animal and configured to communicate with another medical apparatus configured for association with the animal.

13. The medical apparatus of claim 1, wherein the communication module configured to receive communications originating external to the animal includes:
a communication module configured to receive communications originating external to the animal and to receive a communication useful in updating at least one of the threat assessment module or the threat mitigation module.

14. The medical apparatus of claim 1, wherein the threat assessment module includes:
a threat assessment module configured to ascertain a susceptibly of the medical device to a malware threat characteristic of a communication received by the communication module.

15. The medical apparatus of claim 1, wherein the threat assessment module includes:
a threat assessment module configured to ascertain a malware threat characteristic of at least one of a fake communication, a spoofed communication, or a jamming communication received by the communication module.

16. The medical apparatus of claim 1, wherein the threat assessment module includes:
a threat assessment module configured to ascertain a malware threat characteristic of a communication received by the communication module and to initiate a notification to another apparatus of the ascertained threat characteristic.

17. The medical apparatus of claim 1, wherein the threat assessment module includes:
a threat assessment module configured to ascertain a presence of a malware threat of a communication received by the communication module and to ascertain a cessation of the ascertained threat.

18. The medical apparatus of claim 1, wherein the threat assessment module includes:
a threat assessment module configured to be updatable in vivo and configured to ascertain a malware threat characteristic of a communication received by the communication module.

19. The medical apparatus of claim 1, wherein the threat mitigation module includes:
a threat mitigation module configured to implement a selected malware mitigation measure responsive to the ascertained malware threat characteristic of the received communication.

20. The medical apparatus of claim 1, wherein the threat mitigation module includes:
a threat mitigation module configured to implement a malware mitigation measure responsive to the ascertained malware threat characteristic of the received communication and selected in response to a selection algorithm.

21. The medical apparatus of claim 1, wherein the threat mitigation module includes:
a threat mitigation module configured to implement a malware mitigation measure selected based on to a lookup table.

22. The medical apparatus of claim 1, wherein the threat mitigation module includes:
a threat mitigation module configured to implement a malware mitigation measure responsive to the ascertained threat characteristic of the received communication, the malware mitigation measure including at least one of an encryption, an encryption change, a disinformation measure, a change of communication frequency, a change of a schedule of communication, formatting a communication, a communication polarization, a handshake, tunneling, signature, authentication, or verification.

23. The medical apparatus of claim 1, wherein the threat mitigation module includes:
a threat mitigation module configured to be updatable in vivo and configured to implement a malware mitigation measure responsive to the ascertained threat characteristic of the received communication.

24. The medical apparatus of claim 1, wherein the threat mitigation module includes:
a threat mitigation module configured to implement a malware mitigation measure, the malware mitigation measure responsive to the ascertained malware threat characteristic of the received communication and meeting a minimum safety standard for the animal.

25. The medical apparatus of claim 24, wherein the threat mitigation module includes:
a threat mitigation module configured to implement a malware mitigation measure in at least one of the patient module or the communication module, the malware mitigation measure responsive to the ascertained malware threat characteristic of the received communication and meeting a minimum safety standard for the animal.

26. The medical apparatus of claim 24, wherein the threat mitigation module includes:
a threat mitigation module configured to implement a mitigation measure, the mitigation measure responsive to the ascertained threat characteristic of the received communication and predicted to meet a minimum safety standard for the animal.

27. The medical apparatus of claim 24, wherein the threat mitigation module includes:
a threat mitigation module configured to implement a malware mitigation measure, the malware mitigation measure responsive to the ascertained malware threat characteristic of the received communication and selected to provide a least adverse effect on the animal from among two malware mitigation measure.

28. The medical apparatus of claim 24, wherein the threat mitigation module includes:
a threat mitigation module configured to implement a malware mitigation measure, the malware mitigation measure responsive to the ascertained malware threat characteristic of the received communication and predicted by a lookup table as unlikely to have an at least substantial adverse impact on the animal.

29. The medical apparatus of claim 24, wherein the threat mitigation module includes:
a threat mitigation module configured to implement a malware mitigation measure, the malware mitigation measure responsive to the ascertained malware threat characteristic of the received communication and predicted by a lookup table stored in the implanted medical apparatus as unlikely to have an at least substantial adverse impact on the animal.

30. The medical apparatus of claim 1, wherein the threat mitigation module includes:
a threat mitigation module configured to implement a malware mitigation measure, the malware mitigation measure responsive to the ascertained malware threat characteristic of the received communication and unlikely to have an at least substantially serious impact on the animal.

31. The medical apparatus of claim 1, wherein the threat mitigation module includes:
a threat mitigation module configured to implement a malware mitigation measure responsive to the ascertained malware threat characteristic of the received communication and to initiate a notification to another apparatus of the implemented malware mitigation measure.

32. The medical apparatus of claim 1, wherein the threat mitigation module includes:
a threat mitigation module configured to reverse the implementation of the malware mitigation measure.

33. The medical apparatus of claim 1, wherein the threat mitigation module includes:
a threat mitigation module configured to reverse the implementation of the malware mitigation measure and to initiate a notification to another apparatus of the reversing of the implementation of the malware mitigation measure.

34. The medical apparatus of claim 1, further comprising:
a backdoor module configured to respond to a command received from a trusted or a verified third party without regard to the implemented malware mitigation measure responsive to the ascertained threat characteristic of the received communication.

35. The medical apparatus of claim 1, wherein the malware threat characteristic includes a threat characteristic of a blocking communication, a denial of service attack, or a spyware.

36. The medical apparatus of claim 1, wherein the malware threat characteristic includes a threat characteristic of an unauthorized or unregistered executable, a malicious software, a virus, worm, a Trojan horse, or an attack vector.

37. The medical apparatus of claim 1, wherein the malware threat characteristic includes a threat characteristic of a target environment, a carrier object, a transport mechanism, a trigger mechanism, or a defense mechanism.

* * * * *

UNITED STATES PATENT AND TRADEMARK OFFICE
CERTIFICATE OF CORRECTION

PATENT NO. : 9,682,241 B2
APPLICATION NO. : 12/150933
DATED : June 20, 2017
INVENTOR(S) : Roderick A. Hyde et al.

Page 1 of 1

It is certified that error appears in the above-identified patent and that said Letters Patent is hereby corrected as shown below:

In the Claims

In Column 21, Lines 53-54, Claim 14 "to ascertain a susceptibly of the medical device to a" should read --to ascertain a susceptibility of the medical device to a--

In Column 22, Lines 32-33, Claim 21 "based on to a lookup table" should read --based on a lookup table--

In Column 23, Line 14, Claim 27 "from among two malware mitigation measure." should read --from among two malware mitigation measures.--

Signed and Sealed this
Tenth Day of April, 2018

Andrei Iancu
*Director of the United States Patent and Trademark Office*